(12) United States Patent
Couture et al.

(10) Patent No.: US 10,478,243 B2
(45) Date of Patent: Nov. 19, 2019

(54) SURGICAL INSTRUMENTS AND METHODS FOR PERFORMING TONSILLECTOMY AND ADENOIDECTOMY PROCEDURES

(71) Applicant: COVIDIEN LP, Mansfield, MA (US)

(72) Inventors: Gary M. Couture, Ward, CO (US);
Ryan C. Artale, Boulder, CO (US);
John R. Twomey, Superior, CO (US);
Rebecca J. Coulson, Lyons, CO (US);
David J. Van Tol, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 446 days.

(21) Appl. No.: 14/795,660

(22) Filed: Jul. 9, 2015

(65) Prior Publication Data
US 2016/0038225 A1 Feb. 11, 2016

Related U.S. Application Data (60) Provisional application No. 62/035,814, filed on Aug. 11, 2014, provisional application No. 62/035,799, filed on Aug. 11, 2014.

(51) Int. Cl.
*A61B 18/14* (2006.01)
*A61B 17/295* (2006.01)
(Continued)

(52) U.S. Cl.
CPC .......... *A61B 18/1445* (2013.01); *A61B 17/26* (2013.01); *A61B 17/295* (2013.01); *A61B 17/320068* (2013.01); *A61B 2017/2926* (2013.01); *A61B 2017/32007* (2017.08); *A61B 2017/320069* (2017.08);
(Continued)

(58) Field of Classification Search
CPC ............ A61B 18/1442; A61B 18/1445; A61B 18/1447; A61B 2018/145; A61B 2018/1452; A61B 2018/1455; A61B 2018/1457; A61B 2018/1462; A61B 2017/2926
See application file for complete search history.

(56) References Cited

U.S. PATENT DOCUMENTS

D263,020 S 2/1982 Rau, III
D295,893 S 5/1988 Sharkany et al.
(Continued)

FOREIGN PATENT DOCUMENTS

DE 2415263 A1 10/1975
DE 02514501 A1 10/1976
(Continued)

OTHER PUBLICATIONS

Isaacson, Glenn et al.; "Pediatric Tonsillectomy With Bipolar Electrosurgical Scissors", American Journal of Otolaryngology, vol. 19, No. 5 Sep.-Oct. 1998: pp. 291-295.*
(Continued)

*Primary Examiner* — Jaymi E Della
*Assistant Examiner* — Sean W Collins (57) ABSTRACT

A method of surgery includes grasping tissue between tissue-contacting surfaces of first and second jaw members of an end effector assembly, supplying energy to at least one of the tissue-contacting surfaces to treat tissue grasped therebetween, and translating and/or manipulating the end effector assembly to cut tissue in a ripping fashion.

8 Claims, 5 Drawing Sheets

(51) Int. Cl.
*A61B 17/26* (2006.01)
*A61B 18/00* (2006.01)
*A61B 17/32* (2006.01)
*A61B 17/29* (2006.01)

(52) U.S. Cl.
CPC .......... *A61B 2018/00327* (2013.01); *A61B 2018/1452* (2013.01); *A61B 2018/1457* (2013.01)

(56) References Cited

U.S. PATENT DOCUMENTS

| | | | |
|---|---|---|---|
| D295,894 S | 5/1988 | Sharkany et al. | |
| 5,190,541 A | 3/1993 | Abele et al. | |
| D348,930 S | 7/1994 | Olson | |
| 5,613,499 A | 3/1997 | Palmer et al. | |
| D384,413 S | 9/1997 | Zlock et al. | |
| 5,674,220 A | 10/1997 | Fox et al. | |
| 5,700,261 A | 12/1997 | Brinkerhoff | |
| 5,797,958 A * | 8/1998 | Yoon | A61B 17/122 606/139 |
| 5,891,142 A | 4/1999 | Eggers et al. | |
| D424,694 S | 5/2000 | Tetzlaff et al. | |
| D425,201 S | 5/2000 | Tetzlaff et al. | |
| 6,071,281 A * | 6/2000 | Burnside | A61B 18/1482 606/37 |
| 6,174,309 B1 * | 1/2001 | Wrublewski | A61B 18/1442 606/45 |
| D449,886 S | 10/2001 | Tetzlaff et al. | |
| 6,361,534 B1 * | 3/2002 | Chen | A61B 17/2804 606/170 |
| D457,958 S | 5/2002 | Dycus et al. | |
| D457,959 S | 5/2002 | Tetzlaff et al. | |
| 6,425,896 B1 | 7/2002 | Baltschun et al. | |
| D493,888 S | 8/2004 | Reschke | |
| D496,997 S | 10/2004 | Dycus et al. | |
| D499,181 S | 11/2004 | Dycus et al. | |
| D509,297 S | 9/2005 | Wells | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| 7,270,660 B2 | 9/2007 | Ryan | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,621,910 B2 | 11/2009 | Sugi | |
| 7,686,804 B2 | 3/2010 | Johnson et al. | |
| 7,717,914 B2 | 5/2010 | Kimura | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 8,035,129 B2 | 10/2011 | Ramaswamy et al. | |
| 8,112,871 B2 | 2/2012 | Brandt et al. | |
| 8,133,254 B2 | 3/2012 | Dumbauld et al. | |
| 8,162,965 B2 | 4/2012 | Reschke et al. | |
| 8,187,273 B2 | 5/2012 | Kerr et al. | |
| 8,226,650 B2 | 7/2012 | Kerr | |
| 8,251,994 B2 | 8/2012 | McKenna et al. | |
| 8,266,783 B2 | 9/2012 | Brandt et al. | |
| 8,277,446 B2 | 10/2012 | Heard | |
| 8,287,536 B2 | 10/2012 | Mueller et al. | |
| 8,292,067 B2 | 10/2012 | Chowaniec et al. | |
| 8,292,886 B2 | 10/2012 | Kerr et al. | |
| 8,323,310 B2 | 12/2012 | Kingsley | |
| 8,343,150 B2 | 1/2013 | Artale | |
| 8,343,151 B2 | 1/2013 | Siebrecht et al. | |
| 8,357,159 B2 | 1/2013 | Romero | |
| 8,388,647 B2 | 3/2013 | Nau, Jr. et al. | |
| 8,409,247 B2 | 4/2013 | Garrison et al. | |
| 8,430,876 B2 | 4/2013 | Kappus et al. | |
| 8,439,911 B2 | 5/2013 | Mueller | |
| 8,469,991 B2 | 6/2013 | Kerr | |
| 8,469,992 B2 | 6/2013 | Roy et al. | |
| 8,647,343 B2 | 2/2014 | Chojin et al. | |
| 2003/0018332 A1 | 1/2003 | Schmaltz et al. | |
| 2003/0130656 A1 * | 7/2003 | Levin | A61B 18/1442 606/45 |
| 2003/0171747 A1 * | 9/2003 | Kanehira | A61B 17/3201 606/45 |
| 2004/0006340 A1 | 1/2004 | Latterell et al. | |
| 2008/0004616 A1 | 1/2008 | Patrick | |
| 2008/0015567 A1 | 1/2008 | Kimura | |
| 2008/0045947 A1 | 2/2008 | Johnson et al. | |
| 2009/0187188 A1 | 7/2009 | Guerra et al. | |
| 2010/0204697 A1 | 8/2010 | Dumbauld et al. | |
| 2010/0204698 A1 | 8/2010 | Chapman et al. | |
| 2010/0217258 A1 | 8/2010 | Floume et al. | |
| 2010/0249769 A1 | 9/2010 | Nau, Jr. et al. | |
| 2010/0280511 A1 | 11/2010 | Rachlin et al. | |
| 2011/0034918 A1 | 2/2011 | Reschke | |
| 2011/0046623 A1 | 2/2011 | Reschke | |
| 2011/0054468 A1 | 3/2011 | Dycus | |
| 2011/0054471 A1 | 3/2011 | Gerhardt et al. | |
| 2011/0060334 A1 | 3/2011 | Brandt et al. | |
| 2011/0060335 A1 | 3/2011 | Harper et al. | |
| 2011/0071523 A1 | 3/2011 | Dickhans | |
| 2011/0073594 A1 | 3/2011 | Bonn | |
| 2011/0077648 A1 | 3/2011 | Lee et al. | |
| 2011/0082494 A1 | 4/2011 | Kerr et al. | |
| 2011/0118736 A1 | 5/2011 | Harper et al. | |
| 2012/0203272 A1 * | 8/2012 | Wohl | A61B 17/24 606/205 |
| 2013/0274740 A1 * | 10/2013 | Dickson | A61B 18/1442 606/45 |
| 2014/0163552 A1 | 6/2014 | Anderson et al. | |
| 2015/0005760 A1 * | 1/2015 | Poulsen | A61B 18/1206 606/34 |

FOREIGN PATENT DOCUMENTS

| | | |
|---|---|---|
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 202007009317 U1 | 8/2007 |
| DE | 19738457 B4 | 1/2009 |
| DE | 102004026179 B4 | 1/2009 |
| EP | 1159926 A3 | 3/2003 |
| JP | 61-501068 | 9/1984 |
| JP | 6-502328 | 3/1992 |
| JP | 5-5106 | 1/1993 |
| JP | 05-40112 | 2/1993 |
| JP | 06343644 A | 12/1994 |
| JP | 07265328 A | 10/1995 |
| JP | 8-56955 | 3/1996 |
| JP | 08252263 A | 10/1996 |
| JP | 09010223 A | 1/1997 |
| JP | 11-070124 A | 3/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 401367 A1 | 10/1973 |

(56) References Cited

FOREIGN PATENT DOCUMENTS

| WO | 0036986 A1 | 6/2000 |
|---|---|---|
| WO | 0154604 A1 | 8/2001 |
| WO | 2005/110264 A2 | 11/2005 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
PCT Search report and Written Opinion issued in corresponding PCT application No. PCT/US2015/040839 dated May 13, 2016.

\* cited by examiner

SURGICAL INSTRUMENTS AND METHODS FOR PERFORMING TONSILLECTOMY AND ADENOIDECTOMY PROCEDURES

CROSS-REFERENCE TO RELATED APPLICATIONS

This application claims the benefit of, and priority to, U.S. Provisional Patent Application Nos. 62/035,799 and 62/035,814, both of which were filed on Aug. 11, 2014. This application is related to U.S. patent application Ser. No. 14/795,546, filed on Jul. 9, 2015. The entire contents of each of the above applications are hereby incorporated herein by reference.

BACKGROUND

Technical Field

The present disclosure relates to surgical instruments and methods and, more particularly, to surgical instruments and methods for performing tonsillectomy and/or adenoidectomy procedures.

Background of Related Art

The tonsils and adenoids are part of the lymphatic system and are generally located in the back of the throat. These parts of the lymphatic system are generally used for sampling bacteria and viruses entering the body and activating the immune system when warranted to produce antibodies to fight oncoming infections. More particularly, the tonsils and adenoids break down the bacteria or virus and send pieces of the bacteria or virus to the immune system to produce antibodies for fighting off infections.

Inflammation of the tonsils and adenoids (e.g., tonsillitis) impedes the ability of the tonsils and adenoids to destroy the bacteria resulting in a bacterial infection. In many instances, the bacteria remain even after treatment and serve as a reservoir for repeated infections (e.g., tonsillitis or ear infections).

A tonsillectomy and/or adenoidectomy may be performed when infections persist and antibiotic treatments fail. Persistent infection typically leads to enlarged tonsil tissue which may need to be removed since in many cases the enlarged tissue causes airway obstruction leading to various sleep disorders such as snoring or, in some cases, sleep apnea. Some individuals are also born with larger tonsils that are more prone to cause obstruction. An adenoidectomy may also be required to remove adenoid tissue when ear pain persists, or when nose breathing or function of the Eustachian tube is impaired. Often times, tonsillectomy and adenoidectomy procedures are performed at the same time.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

A method of surgery provided in accordance with aspects of the present disclosure includes grasping tissue between tissue-contacting surfaces of first and second jaw members of an end effector assembly, supplying energy to at least one of the tissue-contacting surfaces to treat tissue grasped therebetween, and translating the end effector assembly proximally to cut tissue grasped between the tissue-contacting surfaces in a ripping fashion.

In an aspect of the present disclosure, the first jaw member further includes an insulative member extending towards the second jaw member. The insulative member includes a plurality of crests. Each crest defines a blunt apex and a proximally-facing sharpened edge configured such that, upon grasping tissue, the blunt apexes contact tissue grasped between the tissue-contacting surfaces and, upon translating the end effector assembly proximally, the proximally-facing sharpened edges cut tissue grasped between the tissue-contacting surfaces in a ripping fashion.

In one aspect of the present disclosure, grasping tissue includes grasping tissue disposed between tissue to be removed and wall tissue to remain.

In another aspect of the present disclosure, supplying energy to at least one of the tissue-contacting surfaces includes treating at least a portion of tissue to be removed and at least a portion of wall tissue to remain.

In yet another aspect of the present disclosure, translating the end effector assembly proximally to cut tissue includes separating tissue to be removed from wall tissue to remain.

In still another aspect of the present disclosure, the method further includes removing the tissue to be removed.

Another method of surgery provided in accordance with aspects of the present disclosure includes grasping tissue between tissue-contacting surfaces of first and second jaw members of an end effector assembly. Upon grasping tissue, tissue disposed outside an area defined between the tissue-contacting surfaces is at least partially cut. The method further includes supplying energy to at least one of the tissue-contacting surfaces to treat grasped tissue.

In an aspect of the present disclosure, at least one of the first and second jaw members includes an insulative member extending towards the other jaw member and disposed outside the area. Upon grasping of tissue, the at least one insulative member at least partially cuts tissue disposed outside the area.

In another aspect of the present disclosure, grasping tissue includes grasping tissue disposed between tissue to be removed and wall tissue to remain.

In still another aspect of the present disclosure, at least partially cutting tissue includes cutting tissue disposed between the end effector assembly and tissue to be removed.

In yet another aspect of the present disclosure, the method further includes manipulating the end effector assembly to fully separate tissue to be removed from wall tissue to remain.

In still yet another aspect of the present disclosure, the method further includes removing tissue to be removed.

BRIEF DESCRIPTION OF THE DRAWINGS

Various aspects and features of the present disclosure are described herein with reference to the drawings wherein.

DETAILED DESCRIPTION

Figure 1:
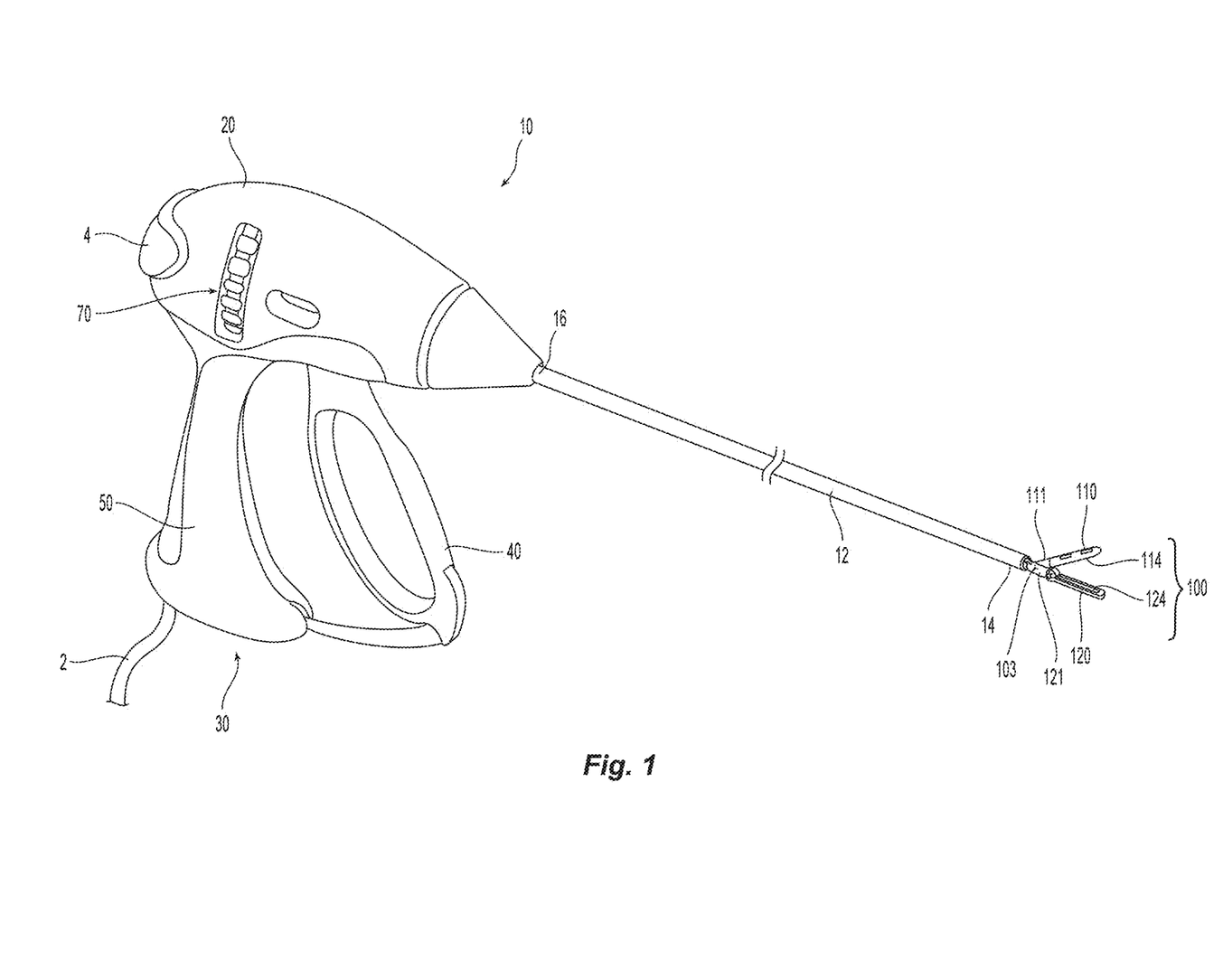
FIG. 1 is a front, side, perspective view of an endoscopic surgical forceps configured for use in accordance with the present disclosure.
Figure 2:
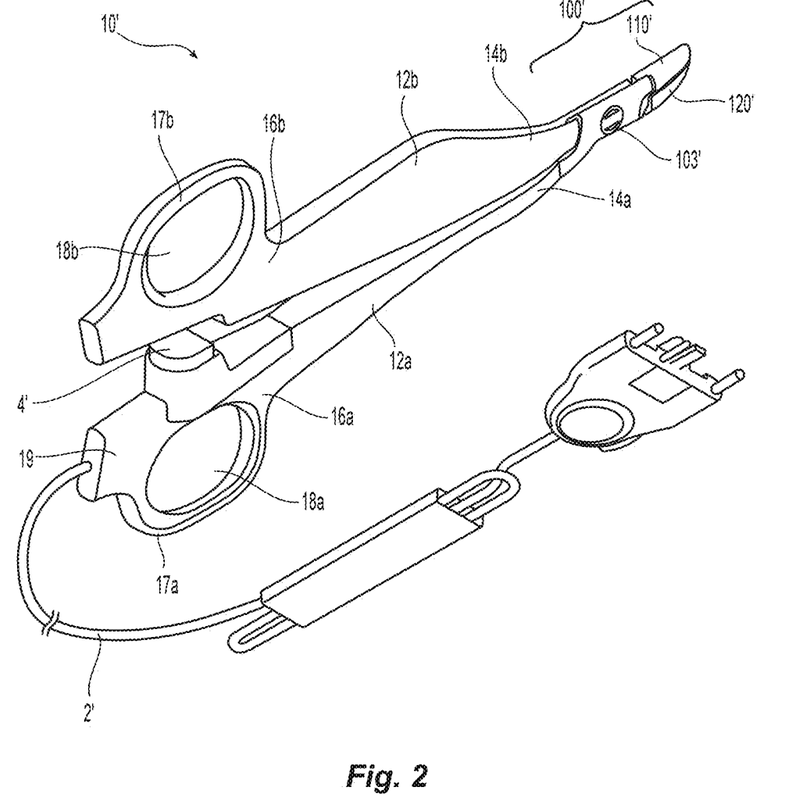
FIG. 2 is a front, side, perspective view of an open surgical forceps configured for use in accordance with the present disclosure.

Turning to FIGS. 1 and 2, FIG. 1 depicts a handheld, shaft-based surgical forceps 10 and FIG. 2 depicts a hemostat-style forceps 10'. For the purposes herein, either forceps 10, forceps 10', or any other suitable surgical instrument may be utilized in accordance with the present disclosure. Obviously, different electrical and mechanical connections and considerations apply to each particular type of instrument; however, the aspects and features of the present disclosure remain generally consistent regardless of the particular instrument used.

Referring to FIG. 1, forceps 10 generally includes a housing 20, a handle assembly 30, a rotating assembly 70, an activation switch 4, and an end effector assembly 100. Forceps 10 further includes a shaft 12 having a distal end 14 configured to mechanically engage end effector assembly 100 and a proximal end 16 that mechanically engages housing 20. Forceps 10 also includes cable 2 that connects forceps 10 to an energy source (not shown), e.g., a generator or other suitable power source, although forceps 10 may alternatively be configured as a battery-powered device. Cable 2 includes a wire (or wires) (not shown) extending therethrough that has sufficient length to extend through shaft 12 in order to provide energy to one or both tissue-contacting plates 114, 124 (FIG. 4) of jaw members 110, 120, respectively. Activation switch 4 is coupled to tissue-contacting plates 114, 124 (FIG. 4) of jaw members 110, 120, respectively, and the source of energy for selectively activating the supply of energy to jaw members 110, 120 for treating, e.g., cauterizing, coagulating/desiccating, and/or sealing, tissue.

Figure 3:
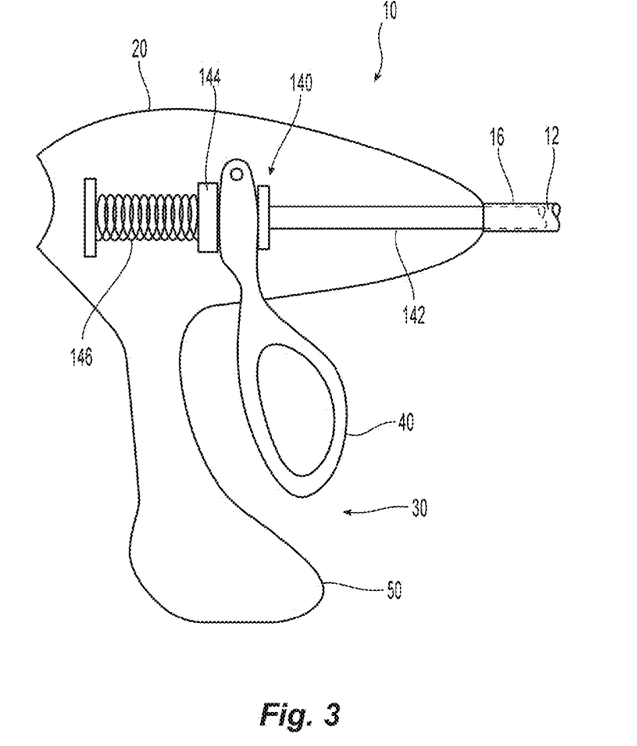
FIG. 3 is a side, cut-away view of the proximal portion of the surgical forceps of FIG. 1, wherein a portion of the housing and some of the internal components thereof have been removed to unobstructively illustrate the handle and drive assemblies of the forceps.
Figure 4:
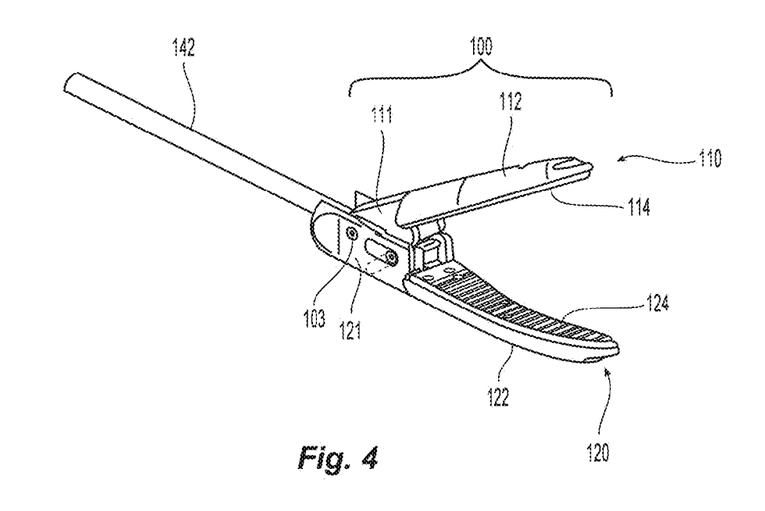
FIG. 4 is a perspective, cut-away view of the distal portion of the surgical forceps of FIG. 1, wherein the shaft has been removed to illustrate the drive bar and end effector assembly of the forceps.

With additional reference to FIGS. 3 and 4, handle assembly 30 includes fixed handle 50 and a movable handle 40. Fixed handle 50 is integrally associated with housing 20 and handle 40 is movable relative to fixed handle 50. Movable handle 40 of handle assembly 30 is operably coupled to a drive assembly 140 that, together, mechanically cooperate to impart movement of one or both of jaw members 110, 120 about a pivot 103 between a spaced-apart position and an approximated position to grasp tissue between jaw members 110, 120. In particular, movable handle 40 is coupled to drive bar 142 via a drive mandrel 144 such that movement of movable handle 40 relative to housing 20 effects longitudinal translation of drive bar 142 through housing 20 and shaft 12. The distal end of drive bar 142 is coupled to one or both jaw members 110, 120 such that longitudinal translation of drive bar 142 relative to end effector assembly 100 pivots one or both of jaw members 110, 120 relative to one another. As shown in FIG. 1, movable handle 40 is initially spaced-apart from fixed handle 50 and, correspondingly, jaw members 110, 120 are disposed in the spaced-apart position. Movable handle 40 is depressible from this initial position to a depressed position corresponding to the approximated position of jaw members 110, 120. Further, a biasing member 146 may be disposed within housing 20 and positioned to bias drive bar 142 distally, thereby biasing jaw members 110, 120 towards the spaced-apart position. However, other configurations are also contemplated.

Referring to FIG. 2, forceps 10' is shown including two elongated shaft members 12a, 12b, each having a proximal end 16a, 16b, and a distal end 14a, 14b, respectively. Forceps 10' is configured for use with an end effector assembly 100' similar to end effector assembly 100 (FIGS. 1 and 4). More specifically, end effector assembly 100' includes first and second jaw members 110', 120' attached to respective distal ends 14a, 14b of shaft members 12a, 12b. Jaw members 110', 120' are pivotably connected about a pivot 103'. Each shaft member 12a, 12b includes a handle 17a, 17b disposed at the proximal end 16a, 16b thereof. Each handle 17a, 17b defines a finger hole 18a, 18b therethrough for receiving a finger of the user. As can be appreciated, finger holes 18a, 18b facilitate movement of the shaft members 12a, 12b relative to one another to, in turn, pivot jaw members 110', 120' from the spaced-apart position, wherein jaw members 110', 120' are disposed in spaced relation relative to one another, to the approximated position, wherein jaw members 110', 120' cooperate to grasp tissue therebetween.

One of the shaft members 12a, 12b of forceps 10', e.g., shaft member 12a, includes a proximal shaft connector 19 configured to connect the forceps 10' to a source of energy (not shown), e.g., a generator. Proximal shaft connector 19 secures a cable 2' to forceps 10' such that the user may selectively supply energy to jaw members 110', 120' for treating tissue and for energy-based tissue cutting. More specifically, an activation switch 4' is provided for supplying energy to jaw members 110', 120' to treat tissue upon sufficient approximation of shaft members 12a, 12b, e.g., upon activation of activation switch 4' via shaft member 12b.

With reference to FIG. 4, end effector assembly 100 of forceps 10 (FIG. 1) is shown, although end effector assembly 100 may similarly be used in conjunction with forceps 10' (FIG. 2), or any other suitable surgical instrument. For purposes of simplicity, end effector assembly 100 is described herein as configured for use with forceps 10 (FIG. 1). Further, end effector assembly 100 is generally described below with reference to FIG. 4, followed by a detailed description, in conjunction with FIGS. 5A-11, of various configurations of end effector assemblies suitable for use in performing tonsillectomy and/or adenoidectomy procedures. Each of these configurations may incorporate the general features of end effector assembly 100 and may likewise be used with forceps 10 (FIG. 1), forceps 10' (FIG. 2), or any other suitable surgical instrument. The general features detailed with respect to end effector assembly 100 (FIG. 4), although applicable to the end effector assemblies of FIGS. 5A-11, will not be repeated for purposes of brevity.

Each jaw member 110, 120 of end effector assembly 100 includes a jaw frame having a proximal flange portion 111, 121, an outer insulative jaw housing 112, 122 disposed about the distal portion (not explicitly shown) of each jaw frame, and a tissue-contacting plate 114, 124, respectively. Proximal flange portions 111, 121 are pivotably coupled to one another about pivot 103 for moving jaw members 110, 120 between the spaced-apart and approximated positions, although other suitable mechanisms for pivoting jaw members 110, 120 relative to one another are also contemplated. The distal portions (not explicitly shown) of the jaw frames are configured to support jaw housings 112, 122, and tissue-contacting plates 114, 124, respectively, thereon.

Outer insulative jaw housings 112, 122 of jaw members 110, 120 support and retain tissue-contacting plates 114, 124 on respective jaw members 110, 120 in opposed relation relative to one another. Tissue-contacting plates 114, 124 are formed from an electrically conductive material, e.g., for conducting electrosurgical energy therebetween for treating tissue, although tissue-contacting plates 114, 124 may alternatively be configured to conduct any suitable energy, e.g., thermal, microwave, light, ultrasonic, etc., through tissue grasped therebetween for energy-based tissue treatment. As mentioned above, tissue-contacting plates 114, 124 are coupled to activation switch 4 (FIG. 1) and the source of energy (not shown), e.g., via the wires (not shown) extending from cable 2 (FIG. 1) through forceps 10 (FIG. 1), such that energy may be selectively supplied to tissue-contacting plate 114 and/or tissue-contacting plate 124 and conducted therebetween and through tissue disposed between jaw members 110, 120 to treat tissue.

Various different configurations of end effector assemblies, similar to end effector assembly 100 (FIG. 4) are detailed below with respect to FIGS. 5A-11. Each of these end effector assemblies is configured to facilitate performing tonsillectomy and/or adenoidectomy procedures, although such end effector assemblies may similarly be beneficial for use in a variety of other procedures. To the extent consistent, any of the features of any of these end effector assemblies may be used in conjunction with any or all of the other end effector assemblies described herein.

Figures 5A, 5B, 6, 7, 8:
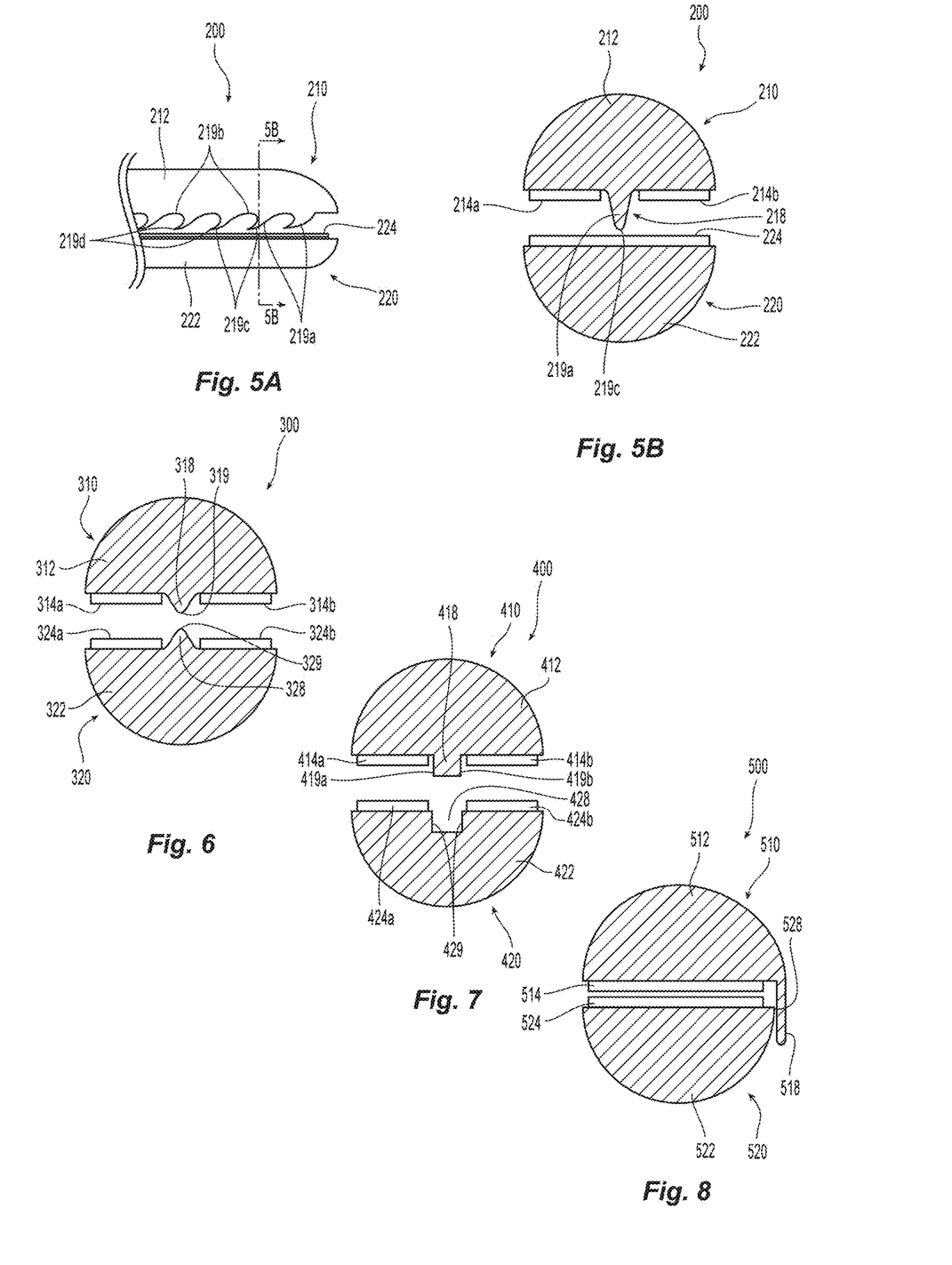
FIG. 5A is a longitudinal, cross-sectional side view of the distal portion of an end effector assembly provided in accordance with the present disclosure and configured for use with the surgical forceps of FIGS. 1 and 2, or any other suitable surgical instrument.
FIG. 5B is a transverse, cross-sectional view of the end effector assembly of FIG. 5A taken along section line "5B-5B" of FIG. 5A.
FIG. 6 is a transverse, cross-sectional view of another end effector assembly provided in accordance with the present disclosure and configured for use with the surgical forceps of FIGS. 1 and 2, or any other suitable surgical instrument.
FIG. 7 is a transverse, cross-sectional view of still another end effector assembly provided in accordance with the present disclosure and configured for use with the surgical forceps of FIGS. 1 and 2, or any other suitable surgical instrument.
FIG. 8 is a transverse, cross-sectional view of yet another end effector assembly provided in accordance with the present disclosure and configured for use with the surgical forceps of FIGS. 1 and 2, or any other suitable surgical instrument.

Turning to FIGS. 5A-5B, end effector assembly 200 includes first and second jaw members 210, 220, respectively. One of the jaw members, e.g., jaw member 220 includes an insulative jaw housing 222 having a substantially planar tissue-contacting plate 224 disposed on the opposing surface thereof. Plate 224 is adapted to connect to a source of energy. The other jaw member, e.g., jaw member 210, includes an insulative jaw housing 212 and a pair of spaced-apart, substantially planar tissue-contacting plates 214a, 214b disposed on the opposing surface thereof. Plates 214a, 214b are likewise adapted to connect to the source of energy. End effector assembly 200 may define a bipolar configuration, wherein plates 214a, 214b are charged to a first electrical potential and plate 224 is charged to a second, different electrical potential such that an electrical potential gradient is created for conducting energy between plates 214a, 214b and plate 224 and through tissue grasped therebetween for treating tissue.

Positioned between the spaced-apart plates 214a, 214b of jaw member 210 is an insulative member 218. More specifically, insulative member 218 extends longitudinally between plates 214a, 214b and towards jaw member 220. Insulative member 218 defines a configuration having a plurality of crests 219a spaced-apart via a plurality of lulls 219b. Each crest 219a defines a blunt apex 219c and a proximally-extending sharpened edge 219d. As a result of this configuration, blunt apexes 219c, not sharpened edges 219d, contact tissue upon movement of jaw members 210, 220 to the approximated position to grasp tissue therebetween. Thus, tissue is not cut during grasping and supplying energy thereto. Insulative member 218 may also function as a stop member to set a minimum gap distance between jaw members 210, 220 in the approximated position. Accordingly, insulative member 218 may be configured to define a height of between about 0.001 inches and about 0.010 inches to achieve a similar minimum gap distance between jaw members 210, 220.

In use, end effector assembly 200, with jaw members 210, 220 disposed in the spaced-apart position, is manipulated into position such that tissue to be treated and cut is disposed between jaw members 210, 220. With respect to tonsillectomy procedures, for example, end effector assembly 200 is positioned between the cavity wall tissue (or other tissue to remain) and the tonsil tissue (or other tissue to be removed). Once the desired position has been achieved, jaw members 210, 220 are moved to the approximated position to grasp tissue therebetween. Thereafter, plates 214a, 214b and plate 224 may be energized to different electrical potentials for conducting energy between plates 214a, 214b and plate 224 and through tissue grasped therebetween to treat the grasped tissue.

Once tissue has been treated, the tissue to be removed, e.g., the tonsil tissue, is separated from the tissue to remain, e.g., the wall tissue. In order to separate the tissue, while maintaining jaw members 210, 220 in the approximated position grasping the previously treated tissue therebetween, end effector assembly 200 is moved proximally relative to tissue. As end effector assembly 200 is moved proximally, sharpened edges 219d of insulative member 218 cut through tissue disposed between the two tissue treatment areas, e.g., the area between plate 214a and the opposed portion of plate 224 and the area between plate 214b and the opposed portion of plate 224, in a "ripping" fashion, thereby separating the tonsil tissue to be removed (on one side of the end effector assembly 200) from the wall tissue to remain (on the other side of end effector assembly 200). The separated tonsil tissue may then be removed using end effector assembly 200, another grasping instrument, a suction device, or via other suitable method.

Turning to FIG. 6, end effector assembly 300 includes first and second jaw members 310, 320, respectively. Each jaw member 310, 320 includes a respective insulative jaw housing 312, 322 and a pair of spaced-apart, substantially planar tissue-contacting plates 314a, 314b and 324a, 324b, respectively. Plates 314a, 314b are positioned to oppose plates 324a, 324b and to grasp tissue therebetween upon movement of jaw members 310, 320 to the approximated position. Plates 314a, 314b and 324a, 324b are adapted to connect to a source of energy. More specifically, end effector assembly 300 may define a bipolar configuration, wherein plates 314a, 314b are charged to a first electrical potential and plates 324a, 324b are charged to a second, different electrical potential such that an electrical potential gradient is created for conducting energy between plates 314a, 314b and plates 324a, 324b and through tissue grasped therebetween for treating tissue.

Positioned between the spaced-apart plates 314a, 314b and 324a, 324b of each jaw member 310, 320, respectively, is an insulative member 318, 328, although in some embodiments only one jaw member 310, 320 includes the insulative member 318, 328. Insulative members 318, 328 extend from jaw members 310, 320 longitudinally between plates 314a, 314b and 324a, 324b, respectively, and towards the other jaw member 320, 310, respectively. Insulative members 318, 328 define generally triangular transverse, cross-sectional configurations with apexes 319, 329, respectively, thereof oriented in opposed relation relative to one another such that apexes 319, 329 meet one another upon full approximation of jaw members 310, 320. Apexes 319, 329 may be sharpened or blunt. Insulative members 318, 328 may further function as stop members to set the minimum gap distance between jaw members 310, 320 in the approximated position. Accordingly, insulative members 318, 328 may cooperate to define a total height, e.g., the sum of the respective heights, of between about 0.001 inches and about 0.010 inches to achieve a similar minimum gap distance between jaw members 310, 320 in the approximated position.

In use, end effector assembly 300, with jaw members 310, 320 disposed in the spaced-apart position, is manipulated into position such that tissue to be treated and cut is disposed between jaw members 310, 320. With respect to tonsillectomy procedures, for example, end effector assembly 300 is positioned between the wall tissue to remain and the tonsil tissue to be removed. Once the desired position has been achieved, jaw members 310, 320 are moved to the approximated position to grasp tissue therebetween. Thereafter, plates 314a, 314b and plates 324a, 324b may be energized to different electrical potentials for conducting energy therebetween and through the grasped tissue to treat the grasped tissue.

Once tissue has been treated, the tonsil tissue is separated from the wall tissue and removed. In order to separate the tonsil tissue, while maintaining jaw members 310, 320 in the approximated position grasping the previously treated tissue therebetween, end effector assembly 300 is manipulated, e.g., translated longitudinally, translated laterally, and/or rotated relative to tissue. As end effector assembly 300 is moved relative to tissue, tissue pinched between apexes 319, 329 is cut or separated via the sharpened apexes 319, 329, in embodiments where so provided, and/or the relatively high pressure concentration on tissue disposed therebetween in a "ripping" fashion. More specifically, the tissue is separated between the two treatment areas, e.g., between plates 314a, 324a on one side of insulative members 318, 328 and between plates 314b, 324b on the other side of insulative members 318, 328, thereby separating the tonsil tissue on one side of end effector assembly 300 and the wall tissue on the other side of end effector assembly 300. The separated tonsil tissue may then be removed similarly as detailed above.

Turning to FIG. 7, end effector assembly 400 includes first and second jaw members 410, 420, respectively. Each jaw member 410, 420 includes a respective insulative jaw housing 412, 422 and a pair of spaced-apart, substantially planar tissue-contacting plates 414a, 414b and 424a, 424b, respectively. Plates 414a, 414b are positioned to oppose plates 424a, 424b and to grasp tissue therebetween upon movement of jaw members 410, 420 to the approximated position. Plates 414a, 414b and 424a, 424b are adapted to connect to a source of energy. More specifically, end effector assembly 400 may define a bipolar configuration, wherein plates 414a, 414b are charged to a first electrical potential and plates 424a, 424b are charged to a second, different electrical potential such that an electrical potential gradient is created for conducting energy between plates 414a, 414b and plates 424a, 424b and through tissue grasped therebetween for treating tissue.

One of the jaw members, e.g., jaw member 410, includes an insulative member 418 extending longitudinally between spaced-apart plates 414a, 414b. Insulative member 418 extends from jaw member 410 towards jaw member 420 and defines a generally rectangular transverse, cross-sectional configuration. As a result of this configuration, insulative member 418 includes a pair of corner edges 419a, 419b which may be sharpened to facilitate cutting tissue. Alternatively, corners 419a, 419b may be angled or curved to define blunt configurations.

The other jaw member, e.g., jaw member 420, includes a recess 428 defined within jaw housing 422 thereof and positioned between spaced-apart plates 424a, 424b. Recess 428 extends longitudinally along jaw member 420 and defines a generally rectangular transverse, cross-sectional configuration that is complementary to the configuration of insulative member 418. More specifically, recess 428 may be similarly sized or slightly larger than insulative member 418 so as to at least partially receive insulative member 418 therein upon approximation of jaw members 410, 420. As a result of this configuration, corner edges 419a, 419b abut or are disposed in close proximity to interior walls 429 defining recess 428 when jaw members 410, 420 are moved to the approximated position.

Insulative member 418 and recess 428 may cooperate to function as a stop member to set a minimum gap distance between jaw members 410, 420 in the approximated position. More specifically, the difference between the height of insulative member 418 and the depth of recess 428 may be selected so as to define a minimum gap distance between jaw members 410, 420 within the ranges detailed above (or other suitable range), when insulative member 418 bottoms out within or is no longer capable of being advanced into recess 428.

In use, end effector assembly 400, with jaw members 410, 420 disposed in the spaced-apart position, is manipulated into position such that tissue to be treated and cut is disposed between jaw members 410, 420. With respect to tonsillectomy procedures, for example, end effector assembly 400 is positioned between the wall tissue to remain and the tonsil tissue to be removed. Once the desired position has been achieved, jaw members 410, 420 are moved to the approximated position to grasp tissue therebetween. At least some tissue cutting or perforation due to shearing of insulative member 418 relative to interior walls 429 of recess 428 may be effected as jaw members 410, 420 are moved to the approximated position. With tissue grasped between plates 414a, 414b and plates 424a, 424b, plates 414a, 414b and plates 424a, 424b may be energized to different electrical potentials for conducting energy therebetween and through the grasped tissue to treat the grasped tissue.

Once tissue has been treated, the tonsil tissue is separated from the wall tissue and removed. In order to separate the tonsil tissue, if not sufficiently separated already, while maintaining jaw members 410, 420 in the approximated position grasping the previously treated tissue therebetween, end effector assembly 400 is manipulated, e.g., translated longitudinally, translated laterally, and/or rotated relative to tissue. As end effector assembly 400 is moved relative to tissue, the partially cut or perforated tissue is pinched between corner edges 419a, 419b of insulative member 418 and interior walls 429 defining recess 428 to further cut and, ultimately separate the tonsil tissue to be removed from the wall tissue to remain in a shearing fashion. The cut-line, similarly as above, is defined between the two treatment areas, e.g., between plates 414a, 424a on one side of insulative member 418 and recess 428 and between plates 414b, 424b on the other side of insulative member 418 and recess 428. The separated tonsil tissue may then be removed similarly as detailed above.

With reference to FIG. 8, end effector assembly 500 includes first and second jaw members 510, 520, respectively. Each jaw member 510, 520 includes an insulative jaw housing 512, 522 having a substantially planar tissue-contacting plate 514, 524 disposed on the opposing surface thereof. Plates 514, 524 are adapted to connect to a source of energy. More specifically, end effector assembly 500 may define a bipolar configuration, wherein plate 514 is charged to a first electrical potential and plate 524 is charged to a second, different electrical potential such that an electrical potential gradient is created for conducting energy between plates 514, 524 and through tissue grasped therebetween for treating tissue.

One of the jaw members, e.g., jaw member 510, defines an increased width as compared to the other jaw member, e.g., jaw member 520, such that a portion of jaw housing 512 overhangs jaw member 520, e.g., is disposed outside the peripheral bounds of jaw member 520. Extending from the overhanging portion of jaw member 510 is an insulative finger 518. Finger 518 extends longitudinally along the outer side edge of jaw housing 512 and extends from jaw housing 512 generally towards jaw member 520. However, due to the fact that jaw housing 512 overhangs jaw member 520, finger 518 extends alongside at least a portion of jaw housing 522 of jaw member 520, outside the tissue grasping area defined between plates 514, 524. Further, finger 518 extends in contact with or close proximity with the corresponding outer peripheral edge 528 of jaw housing 522 of jaw member 520 such that shearing between finger 518 and outer peripheral edge 528 is achieved upon movement of jaw members 510, 520 to the approximated position. Finger 518 may define a sharpened edge to facilitate shear cutting of tissue, or may define a blunt edge.

In use, end effector assembly 500, with jaw members 510, 520 disposed in the spaced-apart position, is manipulated into position such that tissue to be treated and cut is disposed between jaw members 510, 520. With respect to tonsillectomy procedures, for example, end effector assembly 500 is positioned between the wall tissue to remain and the tonsil tissue to be removed with finger 518 disposed adjacent the tonsil tissue to be removed, e.g., spaced-apart from the wall tissue to remain. Once the desired position has been achieved, jaw members 510, 520 are moved to the approximated position to grasp tissue therebetween. At least some tissue cutting or perforation due to shearing of finger 518 relative to outer peripheral edge 528 may be effected as jaw members 510, 520 are moved to the approximated position. Thereafter, plates 514, 524 may be energized to different electrical potentials for conducting energy therebetween and through the grasped tissue to treat the grasped tissue.

Once tissue has been treated, the tonsil tissue is separated from the wall tissue and removed. In order to separate the tonsil tissue, if not sufficiently done so already, while maintaining jaw members 510, 520 in the approximated position grasping the previously treated tissue therebetween, end effector assembly 500 is manipulated, e.g., translated longitudinally, translated laterally, and/or rotated relative to tissue. More specifically, end effector assembly 500 is moved relative to tissue to further cut and ultimately separate the tonsil tissue to be removed from the wall tissue to remain via separating the tissue pinched between finger 518 of jaw member 510 and outer peripheral edge 528 of jaw member 520 in a shearing fashion. In this configuration, the cut-line is disposed on the tissue-to-be-removed side of the tissue treatment area, spaced-apart from the wall tissue to remain. The separated tonsil tissue may ultimately be removed, similarly as detailed above.

Figure 9:
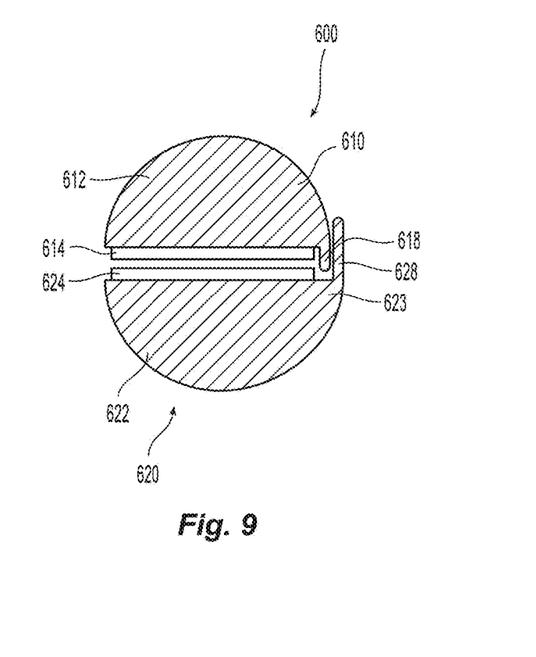
FIG. 9 is a transverse, cross-sectional view of still yet another end effector assembly provided in accordance with the present disclosure and configured for use with the surgical forceps of FIGS. 1 and 2, or any other suitable surgical instrument.

Turning to FIG. 9, end effector assembly 600 generally includes first and second jaw members 610, 620, respectively, each having an insulative jaw housing 612, 622 and a substantially planar tissue-contacting plate 614, 624 disposed on the opposing surface thereof. Plates 614, 624 are adapted to connect to a source of energy and may define a bipolar configuration, similarly as detailed above with respect to end effector assembly 500 (FIG. 8).

One of the jaw members, e.g., jaw member 620, defines an increased width as compared to the other jaw member, e.g., jaw member 610, such that a portion 623 of jaw housing 622 overhangs jaw housing 612 of jaw member 610, e.g., is disposed outside the peripheral bounds of jaw member 610. Extending from portion 623 of jaw member 620 is an outer insulative finger 628, disposed outside the tissue-grasping area defined between plates 614, 624. Outer finger 628 extends longitudinally along the outer side edge of portion 623 of jaw housing 622 and extends from jaw housing 622 generally towards jaw member 610.

Jaw member 610 includes an inner insulative finger 618 disposed outside the tissue-grasping area defined between plates 614, 624 and positioned on the same side as outer finger 628. Inner finger 618 extends longitudinally along the outer side edge of jaw housing 612 and extends from jaw housing 612 towards jaw member 620 opposite portion 623 of jaw member 620. Inner finger 618 defines a reduced height as compared to outer finger 628 to permit full approximation of jaw members 610, 620. Inner and outer fingers 618, 628 are disposed in close proximity or abutment with one another such that, upon movement of jaw members 610, 620 to the approximated position, shear-cutting of tissue disposed between fingers 618, 628 is effected.

As an alternative to being fixedly engaged to jaw housings 610, 620, fingers 618, 628 may be movably coupled to jaw housing 610, 620 via a biasing member (not explicitly shown) to delay the shearing effect of fingers 618, 628 relative to the approximation of jaw members 610, 620. As such, grasping of tissue and, if also desired, initiation of tissue treatment may be effected prior to fingers 618, 628 cutting tissue disposed therebetween. Finger 518 of end effector assembly 500 (see FIG. 8) may also be configured in this manner.

In use, end effector assembly 600, with jaw members 610, 620 disposed in the spaced-apart position, is manipulated into position such that tissue to be treated and cut is disposed between jaw members 610, 620. With respect to tonsillectomy procedures, for example, end effector assembly 600 is positioned between the wall tissue to remain and the tonsil tissue to be removed such that fingers 618, 628 are positioned adjacent the tonsil tissue to be removed. Once the desired position has been achieved, jaw members 610, 620 are moved to the approximated position to grasp tissue therebetween. Moving jaw members 610, 620 to the approximated position affects shear-cutting (or at least partial shear-cutting) of tissue disposed between fingers 618, 628 to at least partially separate the tonsil tissue to be removed from the wall tissue. Thereafter, or overlapping therewith, plates 614, 624 may be energized to different electrical potentials for conducting energy therebetween and through the grasped tissue to treat the grasped wall tissue. The tonsil tissue may be further and fully separated via shearing, if needed, by manipulating end effector assembly 600, and ultimately removed, similarly as above.

Figure 10:
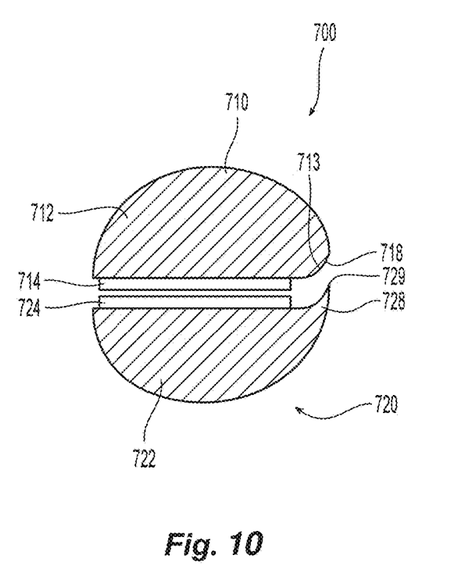
FIG. 10 is a transverse, cross-sectional view of another end effector assembly provided in accordance with the present disclosure and configured for use with the surgical forceps of FIGS. 1 and 2, or any other suitable surgical instrument.

Referring to FIG. 10, end effector assembly 700 includes first and second jaw members 710, 720, respectively. Each jaw member 710, 720 includes an insulative jaw housing 712, 722 having a substantially planar tissue-contacting plate 714, 724 disposed on the opposing surface thereof. Plates 714, 724 are adapted to connect to a source of energy and may define a bipolar configuration, similarly as detailed above.

One of the jaw members, e.g., jaw member 710, includes a longitudinally-extending cut-out 718 defined along one of the outer side edge portions 713 of jaw housing 712 such that one side of jaw housing 712 defines a rounded outer side edge portion 713. The other jaw member, e.g., jaw member 720 defines a tooth 728 extending longitudinally along the outer side edge of jaw housing 722 opposite cut-out 718. Tooth 728 extends from jaw housing 722 generally towards jaw member 710 and defines a sharpened edge 729. Cut-out 718 at least partially accommodates tooth 728 to permit full approximation of jaw members 710, 720. Further, both cut-out 718 and tooth 728 are disposed outside the tissue-grasping area defined between plates 714, 724.

In use, end effector assembly 700, with jaw members 710, 720 disposed in the spaced-apart position, is manipulated into position such that tissue to be treated and cut is disposed between jaw members 710, 720. With respect to tonsillectomy procedures, for example, end effector assembly 700 is positioned between the wall tissue to remain and the tonsil tissue to be removed with tooth 728 positioned adjacent the tonsil tissue to be removed. Once the desired position has been achieved, jaw members 710, 720 are moved to the approximated position to grasp tissue therebetween. Some tissue cutting or perforation via sharpened edge 729 of tooth 728 may be effected as jaw members 710, 720 are moved to the approximated position. Thereafter, plates 714, 724 may be energized to different electrical potentials for conducting energy therebetween and through the grasped tissue to treat the grasped tissue.

Once tissue has been treated, the tonsil tissue is separated from the wall tissue and removed. In order to separate the tonsil tissue, while maintaining jaw members 710, 720 in the approximated position grasping the previously treated tissue therebetween, end effector assembly 700 is manipulated, e.g., translated longitudinally, translated laterally, and/or rotated relative to tissue to cut (or further cut) and ultimately separate the tonsil tissue from the wall tissue in a ripping fashion using sharpened edge 729 of tooth 728. In this configuration, the cut-line, similarly as with end effector assemblies 500, 600 (FIGS. 8 and 9, respectively) is disposed on the tissue-to-be-removed side, e.g., the tonsil tissue side, of the tissue treatment area. The separated tonsil tissue may ultimately be removed, similarly as detailed above.

Figure 11:
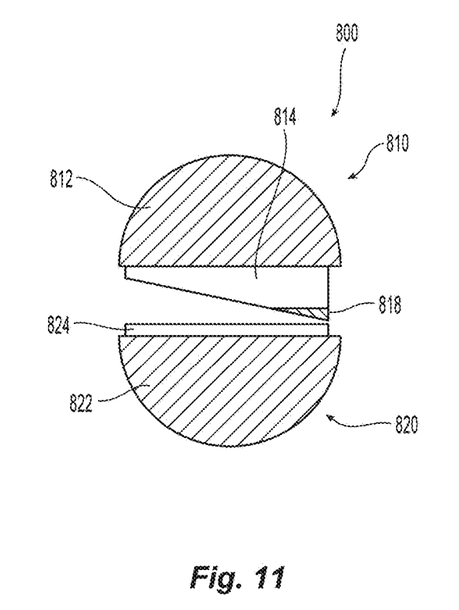
FIG. 11 is a transverse, cross-sectional view of still another end effector assembly provided in accordance with the present disclosure and configured for use with the surgical forceps of FIGS. 1 and 2, or any other suitable surgical instrument.

FIG. 11 illustrates another embodiment of an end effector assembly 800. End effector assembly 800 includes first and second jaw members 810, 820, respectively, each including an insulative jaw housing 812, 822 and a tissue-contacting plate 814, 824 that is adapted to connect to a source of energy. Plates 814, 824 may define a bipolar configuration, similarly as detailed above. The plate of one of the jaw members, e.g., plate 824 of jaw member 820, defines a substantially planar, symmetrical, rectangular transverse cross-sectional configuration. The plate of the other jaw member, e.g., plate 814 of jaw member 810, defines an asymmetrical, triangular transverse cross-sectional configuration wherein plate 814 defines a minimum thickness adjacent a first side thereof and a maximum thickness adjacent a second, opposite side thereof. As a result of this configuration, the tissue-contacting surface of plate 814 is disposed in non-parallel orientation relative to the tissue-contacting surface of plate 824.

A tip portion 818 of plate 814, disposed adjacent the second, maximum thickness side thereof, may include an insulative coating or an insulative cap to maintain electrical isolation between plates 814, 824 in the approximated position of jaw members 810, 820 while also setting the minimum gap distance between jaw members 810, 820 (within the range detailed above). Tip portion 818 may be sharpened to facilitate tissue cutting, although blunt configurations are also contemplated. Tip portion 818 is disposed at the outer boundary of the tissue-grasping area defined between plates 814, 824. As such, substantial tissue treatment is effected only on one side of tip portion 818, e.g., between tip portion 818 and the first, opposite side of plate 814.

In use, end effector assembly 800, with jaw members 810, 820 disposed in the spaced-apart position, is manipulated into position such that tissue to be treated and cut is disposed between jaw members 810, 820. With respect to tonsillectomy procedures, for example, end effector assembly 800 is positioned between the wall tissue to remain and the tonsil tissue to be removed such that tip portion 818 of plate 814 is disposed adjacent the tonsil tissue to be removed. Once the desired position has been achieved, jaw members 810, 820 are moved to the approximated position to grasp tissue therebetween. Some cutting or perforation of tissue disposed between tip portion 818 of plate 814 and plate 824 may be effected as jaw members 810, 820 are moved to the approximated position. Thereafter, plates 814, 824 may be energized to different electrical potentials for conducting energy therebetween and through the grasped tissue to treat the grasped tissue.

Once tissue has been treated, the tonsil tissue is separated from the wall tissue and removed. In order to separate the tonsil tissue, while maintaining jaw members 810, 820 in the approximated position grasping the previously treated tissue therebetween, end effector assembly 800 is manipulated, e.g., translated longitudinally, translated laterally, and/or rotated relative to tissue. As end effector assembly 800 is moved relative to tissue, tissue pinched between tip portion 818 of plate 814 and plate 824 is further cut in a ripping fashion using tip portion 818 to ultimately separate the tonsil tissue to be removed from the wall tissue to remain. As with end effector assemblies 500-700 (FIGS. 8-10, respectively), the cut-line in this configuration is disposed on the tissue-to-be-removed side, e.g., the tonsil tissue side, of the tissue treatment area. The separated tonsil tissue may ultimately be removed, similarly as detailed above.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of surgery, comprising:
   grasping tissue between tissue-contacting surfaces of first and second jaw members of an end effector assembly, wherein the tissue-contacting surface of the second jaw member has the same width as the second jaw member;
   supplying energy to at least one of the tissue-contacting surfaces to treat the tissue that is grasped between the tissue-contacting surfaces of the first and second jaw members of the end effector assembly; and
   cutting adjacent tissue disposed outside of an area defined between the tissue-contacting surfaces with a member extending from the first jaw member, wherein the member is immovably fixed relative to the tissue-contacting surface of the first jaw member, wherein grasping the tissue also affects cutting the adjacent tissue, and wherein cutting the adjacent tissue and supplying the energy are effected during a single grasping of the tissue.

2. The method according to claim 1, wherein the member extending from the first jaw member extends towards the second jaw member and is disposed outside of the area defined between the tissue-contacting surfaces.

3. The method according to claim 1, wherein the tissue that is grasped between the tissue-contacting surfaces of the first and second jaw members of the end effector assembly includes tissue to be removed and wall tissue to remain, and wherein grasping the tissue includes grasping tissue disposed between the tissue to be removed and the wall tissue to remain.

4. The method according to claim 3, further including manipulating the end effector assembly to fully separate the tissue to be removed from the wall tissue to remain.

5. The method according to claim 4, further including removing the tissue to be removed.

6. The method according to claim 1, wherein cutting the adjacent tissue with the member is performed with a blunt, insulative member.

7. A method of surgery, comprising:
   grasping tissue between tissue-contacting surfaces of first and second jaw members of an end effector assembly, the tissue contacting surface of the second jaw member having a width that extends directly from a first outer edge of the second jaw member to a second outer edge of the second jaw member;
   supplying energy to at least one of the tissue-contacting surfaces to treat the tissue that is grasped between the tissue-contacting surfaces of the first and second jaw members of the end effector assembly; and
   cutting adjacent tissue disposed outside of an area defined between the tissue-contacting surfaces with a member extending from the first jaw member, wherein the member is fixed from movement relative to the tissue-contacting surface of the first jaw member, wherein grasping the tissue also affects cutting the adjacent tissue, and wherein supplying the energy is performed after grasping the tissue and after cutting the adjacent tissue.

8. The method according to claim 7, wherein cutting the adjacent tissue with the member is performed with a blunt, insulative member.

* * * * *